(12) United States Patent
Lipkens et al.

(10) Patent No.: US 9,272,234 B2
(45) Date of Patent: Mar. 1, 2016

(54) SEPARATION OF MULTI-COMPONENT FLUID THROUGH ULTRASONIC ACOUSTOPHORESIS

(71) Applicant: FloDesign Sonics Inc., Wilbraham, MA (US)

(72) Inventors: Bart Lipkens, Wilbraham, MA (US); Jason Dionne, Wilbraham, MA (US); Ari Mercado, Wilbraham, MA (US); Brian Dutra, Wilbraham, MA (US); Walter M. Presz, Jr., Wilbraham, MA (US); Thomas J. Kennedy, III, Wilbraham, MA (US); Louis Masi, Wilbraham, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 112 days.

(21) Appl. No.: 13/943,529

(22) Filed: Jul. 16, 2013

(65) Prior Publication Data
US 2013/0302213 A1 Nov. 14, 2013

Related U.S. Application Data

(63) Continuation-in-part of application No. 13/844,754, filed on Mar. 15, 2013.

(60) Provisional application No. 61/671,856, filed on Jul. 16, 2012, provisional application No. 61/611,159, filed on Mar. 15, 2012, provisional application No. 61/611,240, filed on Mar. 15, 2012, provisional application No. 61/754,792, filed on Jan. 21, 2013.

(51) Int. Cl.
*B01D 29/52* (2006.01)
*B01D 43/00* (2006.01)
(Continued)

(52) U.S. Cl.
CPC .............. *B01D 43/00* (2013.01); *C12M 47/02* (2013.01); *B06B 1/0644* (2013.01)

(58) Field of Classification Search
CPC ...... B01D 29/115; B01D 37/00; B01D 29/52; B01D 29/865
USPC ......... 210/748.01–748.05, 321.6–321.9, 542; 209/155, 156; 422/20, 292, 306; 436/177
See application file for complete search history.

(56) References Cited

U.S. PATENT DOCUMENTS 2,473,971 A * 6/1949 Ross .............................. 181/198
2005/0031499 A1* 2/2005 Meier ........................... 422/128
(Continued)

FOREIGN PATENT DOCUMENTS

DE 30 27 433 2/1982
GB 2 420 510 5/2006
(Continued)

OTHER PUBLICATIONS

International Search Report and Written Opinion of International Application No. PCT/US2013/050729 Dated Sep. 25, 2013.

*Primary Examiner* — Walter D Griffin
*Assistant Examiner* — Cameron J Allen
(74) *Attorney, Agent, or Firm* — Richard M. Klein; Fay Sharpe LLP

(57) ABSTRACT

An acoustic standing wave is utilized to separate components from a multi-component fluid, such as oil from an oil-water mixture, in a fluid flow scheme with an acoustophoresis device. For example, the flow scheme and device allows for trapping of the oil as the oil coalesces, agglomerates, and becomes more buoyant than the water.

13 Claims, 17 Drawing Sheets
(2 of 17 Drawing Sheet(s) Filed in Color)

(51) Int. Cl.
*C12M 1/00* (2006.01)
*B06B 1/06* (2006.01)

(56) References Cited

U.S. PATENT DOCUMENTS

2005/0145567 A1* 7/2005 Quintel et al. ............ 210/636
2008/0105625 A1* 5/2008 Rosenberg et al. .......... 210/748
2010/0206818 A1* 8/2010 Leong et al. ............ 210/748.05
2011/0123392 A1 5/2011 Dionne et al.

FOREIGN PATENT DOCUMENTS

WO    WO-87/07178    12/1987
WO    WO-2009/144709    12/2009

* cited by examiner

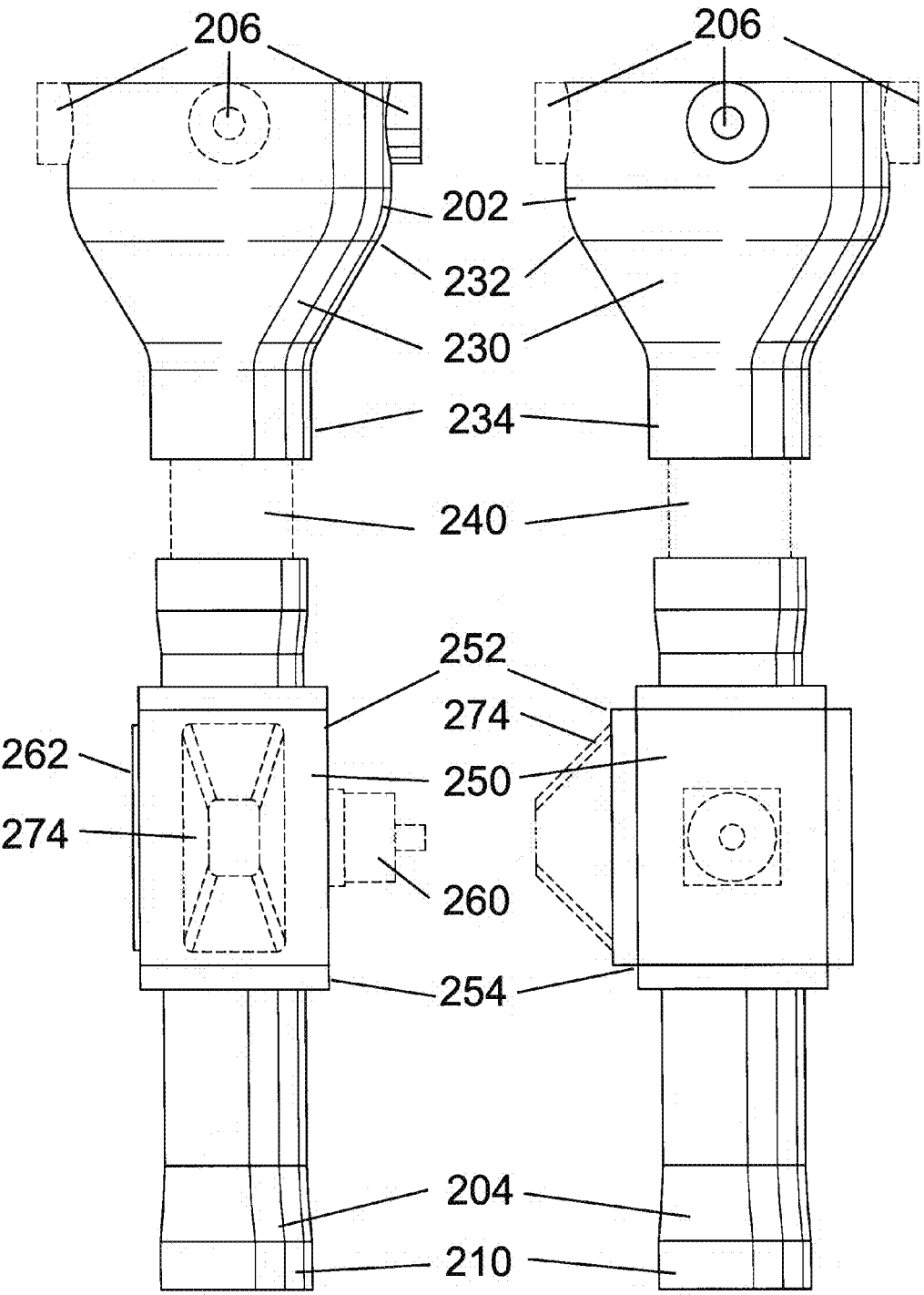

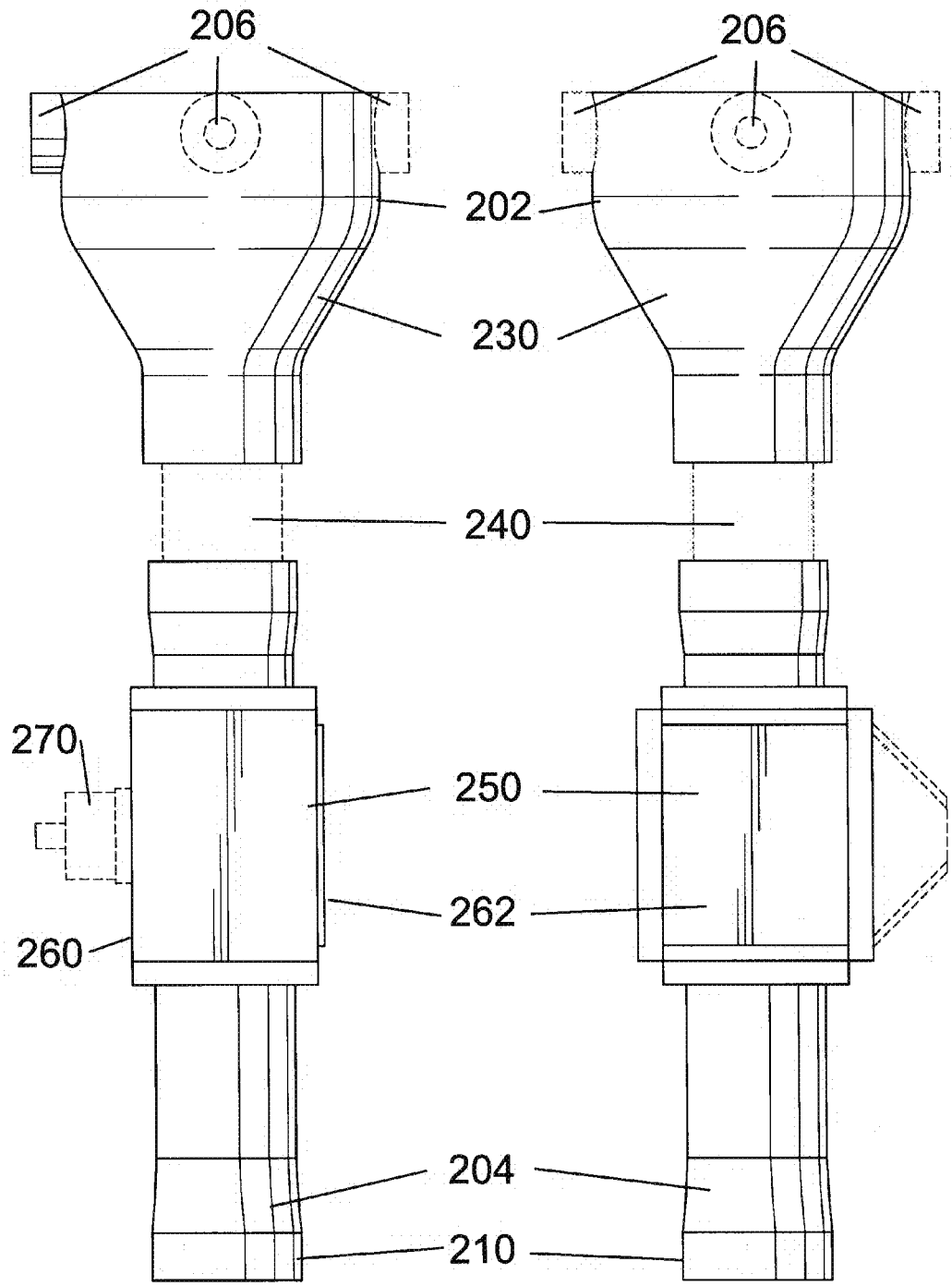

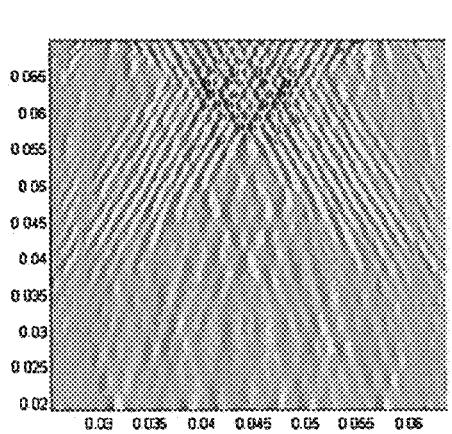 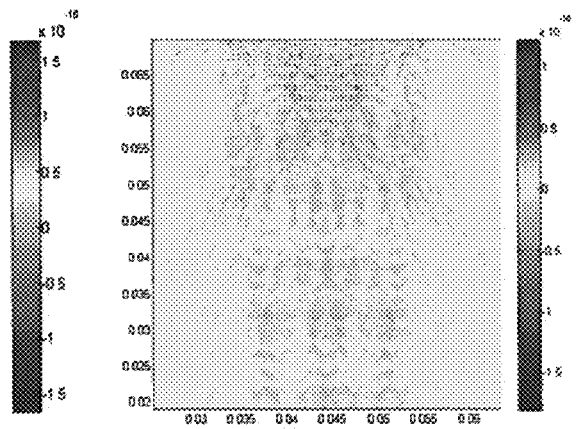
FIG. 26　　　　　　　　　FIG. 27
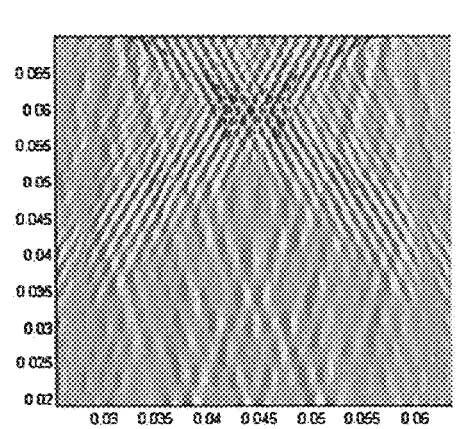 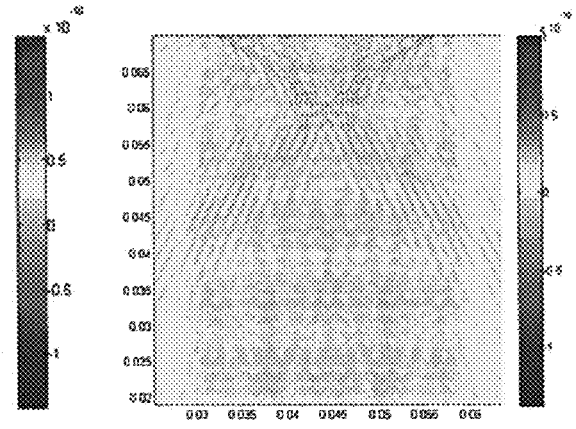
FIG. 28　　　　　　　　　FIG. 29

SEPARATION OF MULTI-COMPONENT FLUID THROUGH ULTRASONIC ACOUSTOPHORESIS

CROSS-REFERENCE TO RELATED APPLICATIONS

This application claims priority to U.S. Provisional Patent Application Ser. No. 61/671,856, filed on Jul. 16, 2012; and is also a continuation-in-part of U.S. Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/754,792, filed Jan. 21, 2013. These applications are incorporated herein by reference in their entireties.

STATEMENT REGARDING FEDERALLY SPONSORED RESEARCH OR DEVELOPMENT

This invention was made with U.S. government support under Phase 1 SBIR Award No. IIP-1215021 awarded by the National Science Foundation. The U.S. government has certain rights in the invention.

BACKGROUND

Many industrial applications generate wastewater that is contaminated with undesirable or hazardous fluid materials, such as oil. These operations include oil drilling, mining and natural gas fracking. Also, spills from oil rigs into seawater generate emulsified oil in the water that is difficult to separate. The use of methods such as hydrocyclones, absorptive media, mechanical filtration, and chemical dispersion to separate the oil from the water are both cost prohibitive and possibly injurious to the environment.

Acoustophoresis is the separation of particles using high intensity sound waves. It has long been known that high intensity standing waves of sound can exert forces on particles. A standing wave has a pressure profile which appears to "stand" still in time. The pressure profile in a standing wave varies from areas of high pressure (nodes) to areas of low pressure (anti-nodes). Standing waves are produced in acoustic resonators. Common examples of acoustic resonators include many musical wind instruments such as organ pipes, flutes, clarinets, and horns.

It would be desirable to provide more effective methods of separating emulsified oil and other contaminants from the contaminated water at reduced cost and low environmental impact.

BRIEF DESCRIPTION

The present disclosure relates to systems and devices for acoustophoresis on preferably a large scale. The devices use one or more unique ultrasonic transducers as described herein, or an array of such transducers. The transducer is driven at frequencies that produce multi-dimensional standing waves.

Disclosed in certain embodiments is an acoustophoresis device, comprising: one or more device inlets at a first end of the device, the first end having a first diameter for receiving fluid flow; a contoured wall downstream of the inlet that narrows the fluid flow to a second diameter of a connecting duct; a flow chamber downstream of the connecting duct, the flow chamber having: an inlet at a first end for receiving the fluid flow, an outlet at a second end opposite the first end, at least one ultrasonic transducer located on a wall of the flow chamber, the ultrasonic transducer including a piezoelectric material driven by a voltage signal to create a multi-dimensional standing wave in the flow chamber, and a reflector located on a wall on the opposite side of the flow chamber from the at least one ultrasonic transducer; a first device outlet located at the first end of the device and separated from the device inlet by a longitudinal sidewall; and a second device outlet located at a second end of the device downstream of the flow chamber outlet.

The device may include a plurality of device inlets spaced about the first end of the device, and the longitudinal sidewall is spaced apart from the contoured wall.

The piezoelectric material of the at least one ultrasonic transducer can have a rectangular shape. The reflector can have a non-planar surface.

In particular embodiments, the first end of the device has a circular cross-section and the flow chamber has a rectangular cross-section.

The multi-dimensional standing wave generated by the transducer can result in an acoustic radiation force having an axial force component and a lateral force component that are of the same order of magnitude.

In embodiments, the transducer comprises: a housing having a top end, a bottom end, and an interior volume; and a crystal at the bottom end of the housing having an exposed exterior surface and an interior surface, the crystal being able to vibrate when driven by a voltage signal.

Sometimes, no backing layer is present within the housing, and an air gap is present in the interior volume between the crystal and a top plate at the top end of the housing.

In other devices, the transducer further comprises a backing layer contacting the interior surface of the crystal, the backing layer being made of a substantially acoustically transparent material. The substantially acoustically transparent material can be balsa wood, cork, or foam. The substantially acoustically transparent material may have a thickness of up to 1 inch.

The flow chamber can further comprise a transparent window for viewing the interior of the flow chamber.

In particular embodiments, the device has a length L from the at least one device inlet to a bottom of the longitudinal sidewall, and a ratio of the length L to the first diameter is less than 1.

These and other non-limiting characteristics are more particularly described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIG. 3 is a right side view of the device of FIG. 1.

FIG. 4 is a front view of the device of FIG. 1.

FIG. 5 is a rear view of the device of FIG. 1.

FIG. 6 is a left side view of the device of FIG. 1.

FIG. 26 shows the lateral force component at a resonance frequency of 2.0106 MHz.

FIG. 27 shows the axial acoustic radiation force component at a resonance frequency of 2.0106 MHz.

FIG. 28 shows the lateral force component at a resonance frequency of 2.025 MHz.

FIG. 29 shows the axial acoustic radiation force component at a resonance frequency of 2.025 MHz.

DETAILED DESCRIPTION

Figure 1:
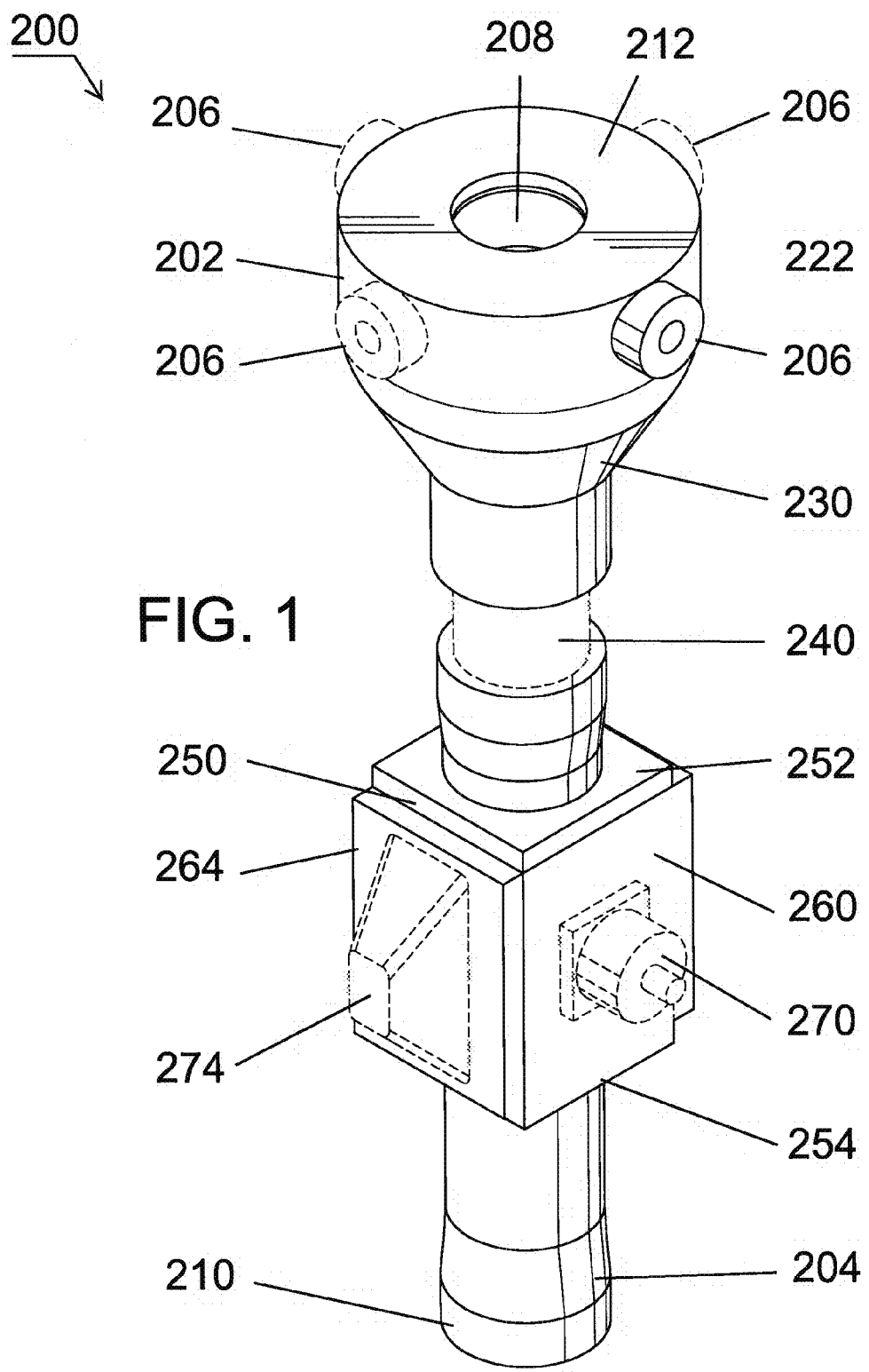
FIG. 1 is a front top perspective view of an exemplary embodiment of a device of the present disclosure.
Figure 2:
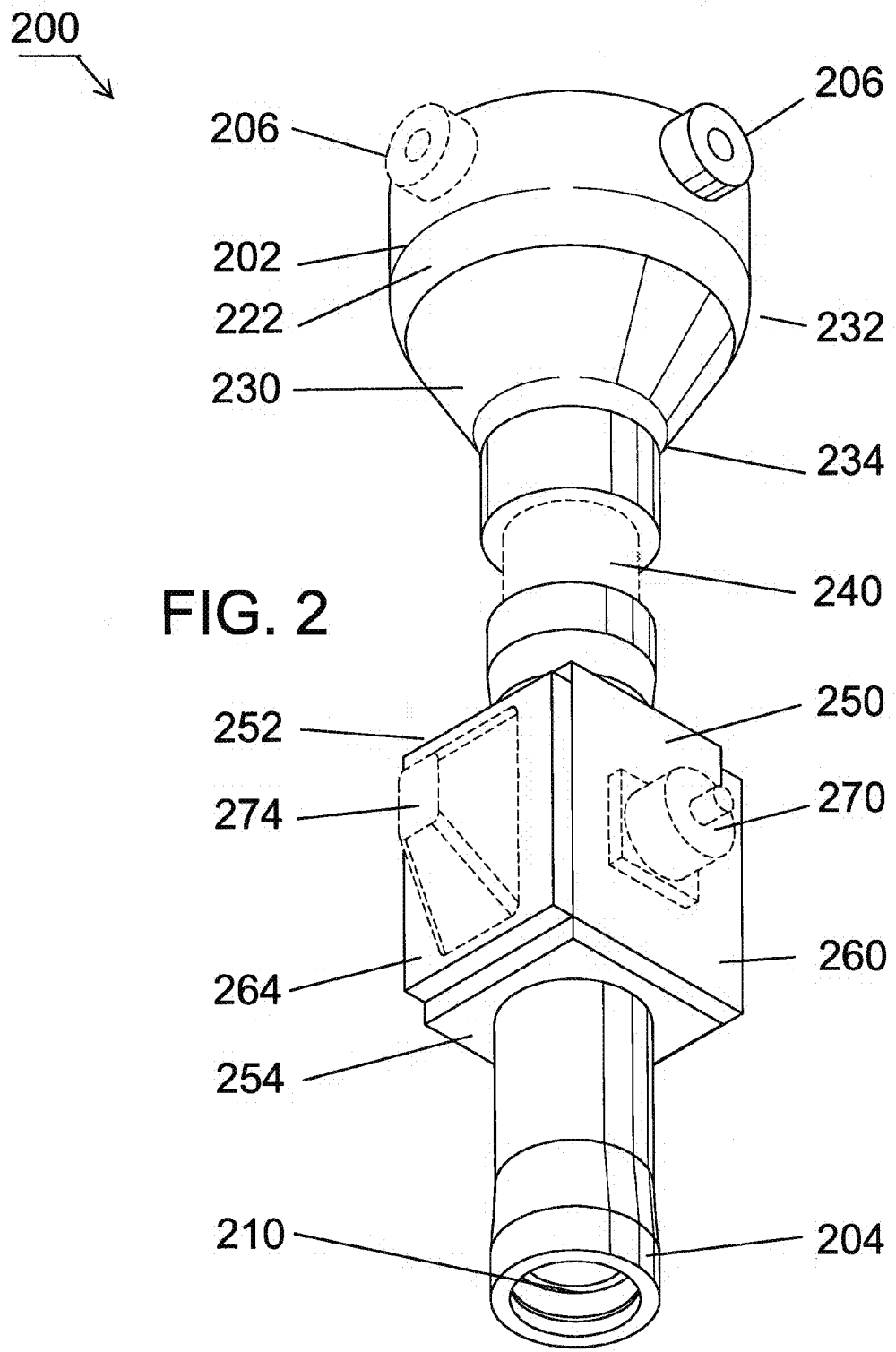
FIG. 2 is a front bottom perspective view of the device of FIG. 1.
Figure 7:
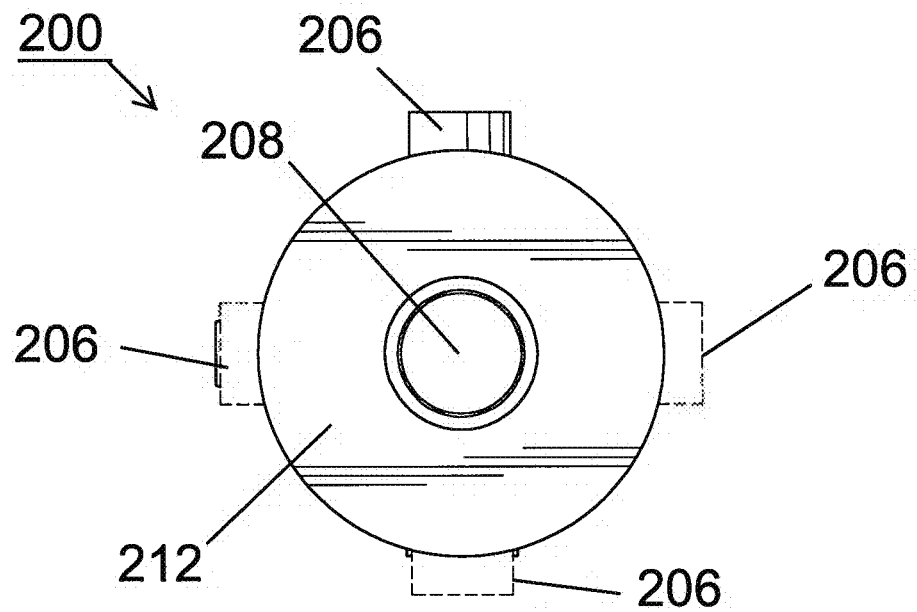
FIG. 7 is a top view of the device of FIG. 1.
Figure 8:
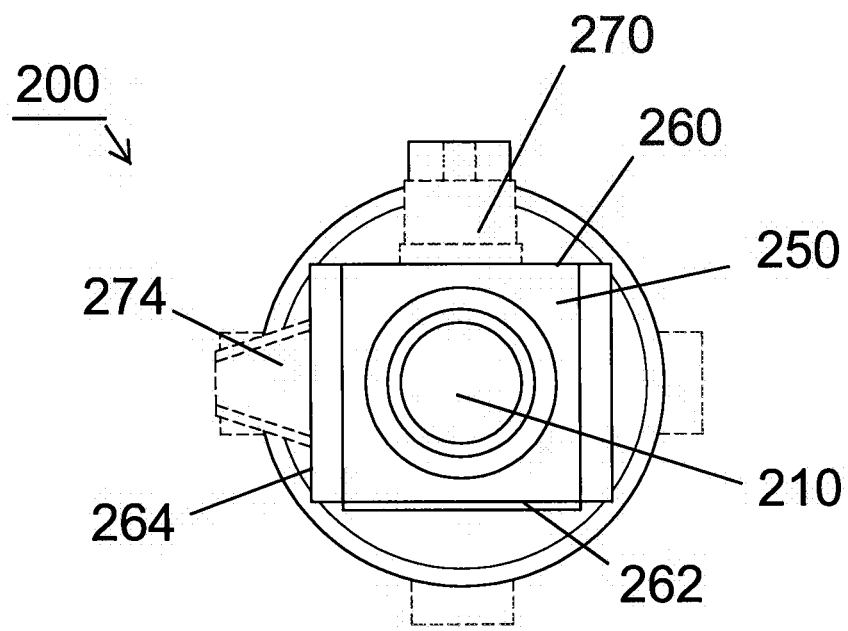
FIG. 8 is a bottom view of the device of FIG. 1.
Figure 9:
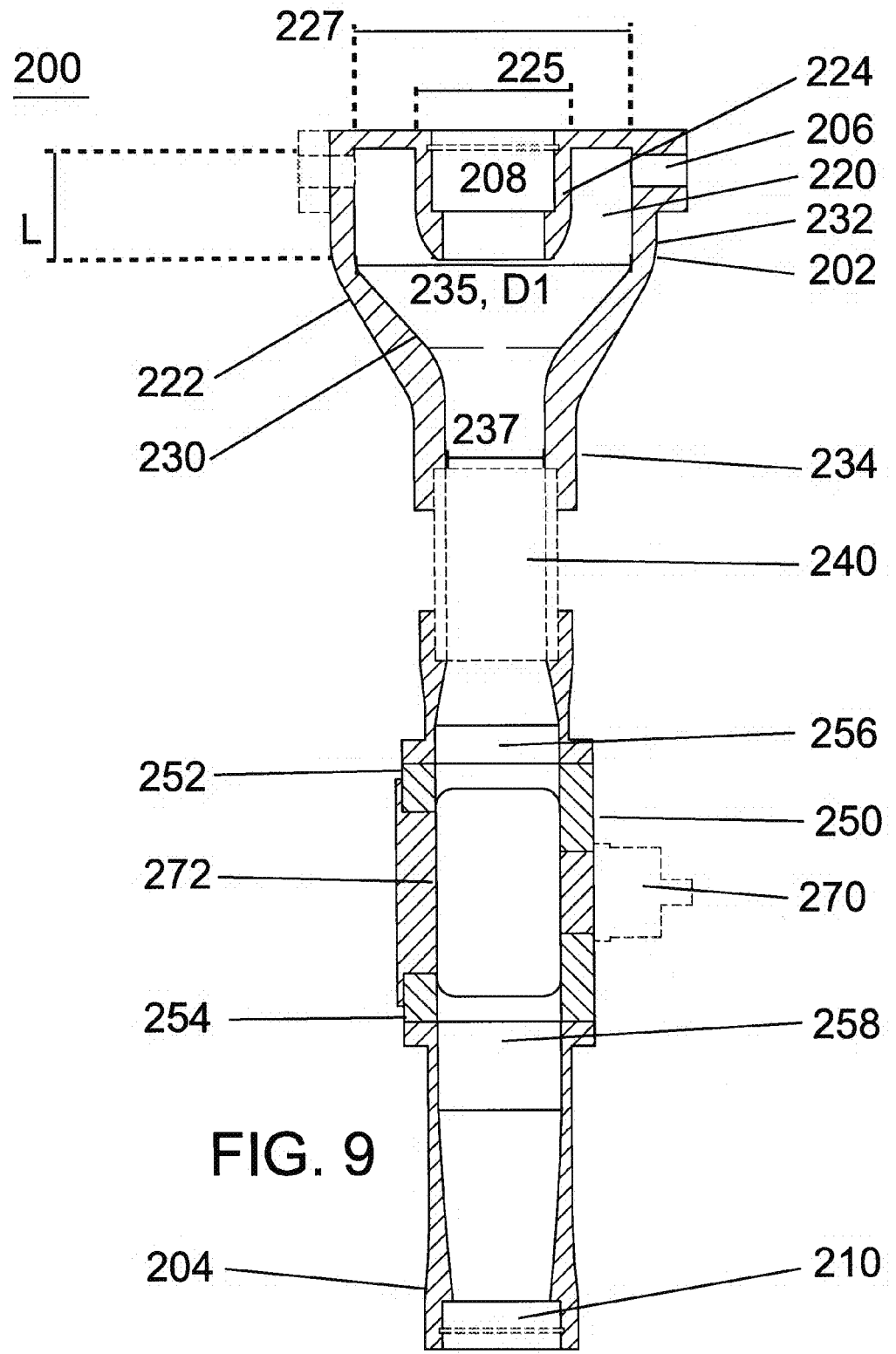
FIG. 9 is a right side cross-sectional view of the device of FIG. 1.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of."

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

Efficient separation technologies for multi-component liquid streams that eliminate any waste and reduce the required energy, and therefore promote a sustainable environment, are needed. Large volume flow rate acoustophoretic phase separator technology using ultrasonic standing waves provides the benefit of having no consumables, no generated waste, and a low cost of energy. The technology is efficient at removal of particles of greatly varying sizes, including separation of micron and sub-micron sized particles. Examples of acoustic filters/collectors utilizing acoustophoresis can be found in commonly owned U.S. patent application Ser. Nos. 12/947,757; 13/085,299; 13/216,049; and 13/216,035, the entire contents of each being hereby fully incorporated by reference. Generally, an acoustophoretic system employs ultrasonic standing waves to trap (i.e. hold stationary) secondary phase particles, gases, or liquids that are suspended in a host fluid stream. The secondary phase can be continuously separated out of the host fluid as the mixture flows through the acoustophoretic system.

The platform technology described herein provides an innovative solution that includes a large volume flow rate acoustophoretic phase separator based on ultrasonic standing waves with the benefit of having no consumables, no generated waste, and a low cost of energy. Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the present disclosure provides systems that operate at the macro-scale for separations in flowing systems with high flow rates. The acoustic resonator is designed to create a high intensity three dimensional ultrasonic standing wave that generates three dimensional pressure gradients and results in an acoustic radiation force that is larger than the combined effects of fluid drag and buoyancy or gravity, and is therefore able to trap (i.e., hold stationary) the suspended phase to allow more time for the acoustic wave to increase particle concentration, agglomeration and/or coalescence. The present systems have the ability to create ultrasonic standing wave fields that can trap particles in flow fields with a linear velocity ranging from 0.1 mm/sec to velocities exceeding 1 cm/s. This technology offers a green and sustainable alternative for separation of secondary phases with a significant reduction in cost of energy. Excellent particle separation efficiencies have been demonstrated for particle sizes as small as one micron.

This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the acoustic forces on the trapped particles results in concentration, agglomeration and/or coalescence of particles and droplets. Particles which are denser than the host fluid are separated through enhanced gravitational settling, and particles which are less dense than the host fluid are separated through enhanced buoyancy.

Efficient and economic particle separation processes can be useful in many areas of energy generation, e.g., producing water, hydro-fracking, and bio-fuels, e.g., harvesting and dewatering. Acoustophoretic technology can be used to target accelerated capture of bacterial spores in water, oil-recovery, and dewatering of bio-oil derived from micro-algae. Current technology used in the oil recovery field does not perform well in recovery of small, i.e., less than 20 micron, oil droplets. However, the acoustophoretic systems described herein can enhance the capture and coalescence of small oil droplets, thereby shifting the particle size distribution resulting in an overall increased oil capture. To be useful, it is generally necessary to demonstrate large flow rates at a level of 15-20 gallons per minute (GPM) per square foot (cross-sectional area). Another goal is the increased capture of oil droplets with a diameter of less than 20 microns. Much prior work on acoustophoretics only occurred at the microscale, in MEMS applications in research settings. Industrial processes require high flow rates and continuous operation.

Acoustophoretic separation can also be used to aid such applications as advanced bio-refining technology to convert low-cost readily available non-food biomass (e.g. municipal solid waste and sewage sludge) into a wide array of chemicals and secondary alcohols that can then be further refined into renewable gasoline, jet fuel, or diesel. A water treatment technology is used to de-water the fermentation broth and isolate valuable organic salts for further processing into fuels. The dewatering process is currently done through an expensive and inefficient ultra-filtration method that suffers from frequent fouling of the membranes, a relatively low concentration factor, and a high capital and operating expense. Acoustophoretic separation can filter out particles with an incoming particle size distribution that spans more than three orders of magnitude, namely from 600 microns to 0.3 microns, allowing improvements in the concentration of the separated broth with a lower capital and operational expense.

Acoustophoretic separation is also useful for the harvesting, oil-recovery, and dewatering of micro-algae for conversion into bio-oil. Current harvesting, oil recovery, and dewatering technologies for micro-algae suffer from high operational and capital expenses. Current best estimates put the price of a barrel of bio-oil derived from micro-algae at a minimum of $200.00 per barrel. There is a need in the art of micro-algae biofuel for technologies that improve harvesting, oil-recovery, and dewatering steps of this process. Acoustophoretic separation technology meets this need.

Some other applications are in the areas of wastewater treatment, grey water recycling, and water production. Other applications are in the area of biopharmaceuticals, life sciences, and medical applications, such as the separation of lipids from red blood cells. This can be of critical importance during cardiopulmonary bypass surgery, which involves suctioning shed mediastinal blood. Lipids are unintentionally introduced to the bloodstream when blood is re-transfused to the body. Lipid micro-emboli can travel to the brain and cause various neuro-cognitive disorders. Therefore, there is a need to cleanse the blood. Existing methods are currently inefficient or harmful to red blood cells.

Particular embodiments focus on the capture and growth of sub 20 micron oil droplets. At least 80% of the volume of sub-20-micron droplets are captured and then grown to droplets that are bigger than 20 microns. The process involves the trapping of the oil droplets in the acoustic standing wave, coalescence of many small trapped droplets, and eventually release of the larger droplets when the acoustic trapping force becomes smaller than the buoyancy force.

Desirably, the ultrasonic transducers generate a three-dimensional standing wave in the fluid that exerts a lateral force on the suspended particles/secondary fluid to accompany the axial force so as to increase the particle trapping capabilities of a acoustophoretic system. Typical results published in literature state that the lateral force is two orders of magnitude smaller than the axial force. In contrast, the technology disclosed in this application provides for a lateral force to be of the same order of magnitude as the axial force.

The present disclosure relates to the use of an acoustic standing wave generated by an ultrasonic transducer or transducers to separate oil from processed water on a macro scale. The oil may be partially emulsified with the water. The separation occurs by trapping the oil particles at the pressure nodes and anti-pressure nodes in a standing wave. As the oil is trapped at these nodes, it agglomerates and, due to buoyancy, will move to an area of trapped, concentrated oil. The buoyancy separation is accomplished through fluid dynamics with the main fluid stream flowing in a downward direction and the trapped, agglomerated and coalesced oil particles floating upward, due to buoyancy, into a trap.

The oil particles are separated from the fluid stream at the anti-pressure nodes of the acoustic standing wave due to the difference in their acoustic contrast factors from the fluid stream. The equation for determining the acoustic contrast factor of an oil in a fluid is known, and is related to the density of the fluid, the density of the oil in the fluid, the compressibility of the fluid, and the compressibility of the oil in the fluid. Both oil and emulsified oil typically have a negative contrast factor ($\phi$).

In the present disclosure, a 3-D acoustic standing wave is generated by causing the ultrasonic transducer to act in a "drumhead" fashion as opposed to a "piston" fashion. The "drumhead" operation of the piezoelectric element in the ultrasonic transducer causes multiple standing waves to be generated in a 3-D space. This is opposed to the action of the piezoelectric crystal in the ultrasonic transducer acting in a "piston" fashion n where a single standing wave is produced. Through the use of a 3-D multi-standing wave, macro-scale trapping of oil particles may be accomplished. This allows for high volumes of processed water to be treated and the oil to be separated from the water, The piezoelectric crystal in the ultrasonic transducer may be directly interfaced with the fluid stream or may have a protective layer or matching layer over the surface of the piezoelectric crystal that is interfaced with the fluid stream, The protective layer may be a coating, such as a polyurethane or epoxy. The protective layer may also be plated onto the surface of the piezoelectric crystal that is interfaced with the fluid stream. The plated layer may be added to the surface of the piezoelectric crystal through either electrolytic or electroless plating. The plating material may be nickel, chrome, copper, indium or combination of layers of these materials. Also, the secondary material or matching layer may be adhered to the surface of the piezoelectric crystal such that the matching layer is now interfaced with the fluid stream. The matching layer may be a material such as a stainless steel that is adhered to the piezoelectric crystal through the use of a two-part epoxy system.

FIGS. 1-9 show various views of an acoustophoresis device of the present disclosure. Generally, the acoustophoresis device uses the ultrasonic transducer to separate suspended oil particles/droplets in a fluid stream into ordered, coalesced and agglomerated particles trapped in a standing wave of the acoustophoresis device. The flow of the fluid stream is from the upper end downward (i.e. with gravity). The fluid stream can enter the device through one of many inlets that surround a central trapping device for the agglomerated and separated oil. The fluid stream flows into the acoustophoresis separation device from a pump through the inlet. The agglomerated and coalesced oil gains buoyancy and rises into the central oil trapping device. The device is shown here in an orientation where the flow direction is downwards, which is used for separating less-dense particles from the host fluid. However, the device may be essentially turned upside down to allow separation of particles which are heavier than the host fluid. Instead of a buoyant force in an upward direction, the weight of the agglomerated particles due to gravity pulls them downward.

The initial fluid stream is made up of a host fluid (e.g. water) and a suspended phase (e.g. oil droplets/articles). The fluid stream enters the device 200 through one or more device inlets 206 into an annular plenum 220 at a first end 202 of the device. The first end 202 includes an outer sidewall 222 and an inner longitudinal sidewall 224. An end wall 212 is also visible, from which the longitudinal sidewall extends. The term "annular," as used herein, only designates the area or volume between the outer sidewall and the inner longitudinal sidewall, and should not be construed as requiring the first end of the device to have a circular cross-section. However, in contemplated embodiments the first end of the device has a circular cross-section. The annular plenum has an inner diameter 225 and an outer diameter 227. This construction guides the fluid stream flow downwards in the direction of the centerline, i.e. with little to no radial or circumferential motion component. This helps to create laminar/plug flow later downstream. One device inlet 206 is shown here, with three other inlets spaced about the first end being shown in dotted line. It is contemplated that any number of inlets may be provided as desired. In particular embodiments, four inlets are used. The inlets are radially oriented.

A contoured nozzle wall 230 reduces the outer diameter of the flow path, which generates higher velocities near the wall and reduces turbulence, producing near plug flow as the fluid velocity profile develops and the fluid passes through the connecting duct and into a flow/separation chamber. The contoured wall also adds a radial motion component to the suspended particles, moving the particles closer to the centerline of the device and generating more collisions with rising, buoyant agglomerated particles. This radial motion will allow for optimum scrubbing of the particles from the fluid in the connecting duct prior to reaching the separation chamber. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension. The contoured nozzle wall directs the fluid in a manner that generates large scale vortices at the entrance of the first device outlet to also enhance particle collection. Generally, the flow area of the device is designed to be continually decreasing from the device inlets to the separation chamber to assure low turbulence and eddy formation for better particle separation, agglomeration, and collection. Put another way, the contoured wall 230 has a wide end 232 and a narrow end 234. The first end of the device/the wide end of the nozzle wall has a first diameter 235, and the narrow end of the nozzle wall has a second diameter 237. The second diameter is less than the first diameter. The connecting duct 240 is downstream of the nozzle wall and connects to the inlet 256 of the flow chamber 250.

The flow/separation chamber 250 is downstream of the connecting duct 240 and has an inlet 256 at a first end 252, and an outlet 258 at a second end 254 opposite the first end. At least one ultrasonic transducer 270 is present on a wall 260, and a reflector 272 is located on a wall 262 opposite the transducer. Multiple transducers can be used, as desired. In use, standing waves are created between the transducer 270 and reflector 272. These standing waves can be used to agglomerate particles, and this orientation is used to agglomerate particles that are buoyant (e.g. oil). Fluid, containing residual particles, then exits through the flow chamber outlet 258 and through a second device outlet 210 located at a second end 204 of the device opposite the first end 202 of the device. Also shown here is a transparent window 274 on a third wall 264 of the flow chamber. It is contemplated that in particular embodiments, the flow chamber has a rectangular cross-section. The flow chamber inlet and outlets have a circular cross-section for interfacing with the other components of the device.

As the buoyant particles agglomerate, they eventually overcome the combined effect of the fluid flow drag forces and acoustic radiation force, and their buoyant force is sufficient to cause the buoyant particles to rise upwards. In this regard, a first device outlet or collection duct 208 is present at the first end of the device 202, and is surrounded by the longitudinal sidewall 224, or put another way is separated from the device inlets 206 by the longitudinal sidewall 224, or put yet another way the first device outlet is a hole in the end wall 212. The agglomerated buoyant particles exit the device through the first device outlet 208. The first device outlet and the second device outlet are on opposite ends of the device.

It should be noted that the buoyant particles formed in the separation chamber 250 subsequently pass through the connecting duct 240. This causes the incoming fluid stream flow from the device inlets 206 to flow over the rising agglomerated particles due to the inward radial motion imparted by the contoured wall 230. This allows the rising particles to also trap smaller particles in the incoming flow, increasing scrubbing effectiveness. The length of the connecting duct and the contoured nozzle wall thus increase scrubbing effectiveness. Especially high effectiveness is found for particles with a size of 0.1 microns to 10 microns, where efficiency is very low for conventional methods. As noted here, the distance from the device inlets 206 to the bottom of the longitudinal sidewall 224 is marked as length (L). The first diameter is marked as D1 (reference numeral 235). This length-to-diameter ratio here (i.e. L/D1) is less than 1.

The design here results in low flow turbulence at the flow chamber inlet, a scrubbing length before (i.e. upstream of) the flow chamber to enhance particle agglomeration and/or coalescence before acoustic separation, and the use of the collection vortices to aid particle removal upstream of the flow chamber.

The ultrasonic transducer(s) are arranged to cover the entire cross-section of the fluid stream flowpath. In certain embodiments, the flow chamber has a square cross section of 6 inches×6 inches which operates at flow rates of up to 3 gallons per minute (GPM), or a linear velocity of 8 mm/sec. The transducer can be a PZT-8 (Lead Zirconate Titanate) transducer with a 1-inch diameter and a nominal 2 MHz resonance frequency. Each transducer consumes about 28 W of power for droplet trapping at a flow rate of 3 GPM. This translates in an energy cost of 0.25 kW hr/m$^3$. This is an indication of the very low cost of energy of this technology. Desirably, when multiple transducers are present, each transducer is powered and controlled by its own amplifier. This device shifts the particle size distribution in the host fluid through agglomeration of smaller oil droplets into larger oil droplets.

Figure 10:
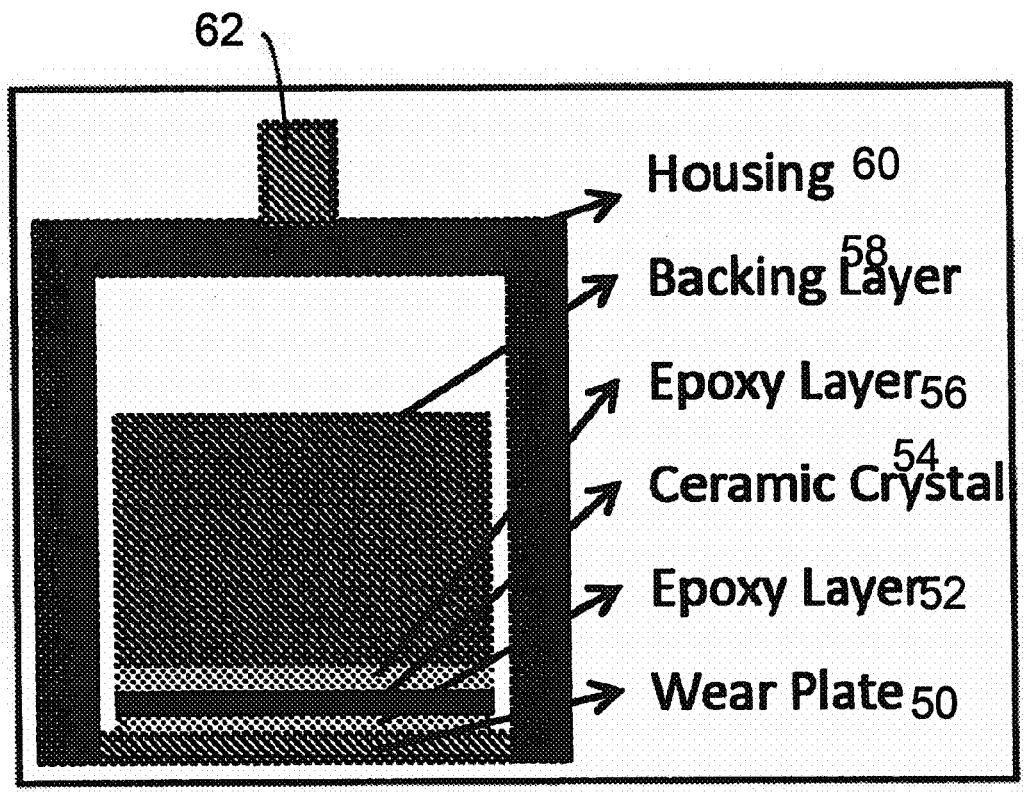
FIG. 10 is a cross-sectional diagram of a conventional ultrasonic transducer.

FIG. 10 is a cross-sectional diagram of a conventional ultrasonic transducer. This transducer has a wear plate/protective layer 50 at a bottom end, epoxy layer 52, piezoelectric material 54 (made of, e.g. PZT), an epoxy layer 56, and a backing layer 58. The epoxy layer 56 attaches backing layer 58 to the crystal 54. The entire assembly is contained in a housing 60 which may be made out of, for example, aluminum. A connector 62 provides connection for wires to pass through the housing and connect to leads (not shown) which attach to the piezoelectric material 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates, and face in the direction in which the wave is generated. The piezoelectric material can be, for example, a ceramic crystal.

Figure 11:
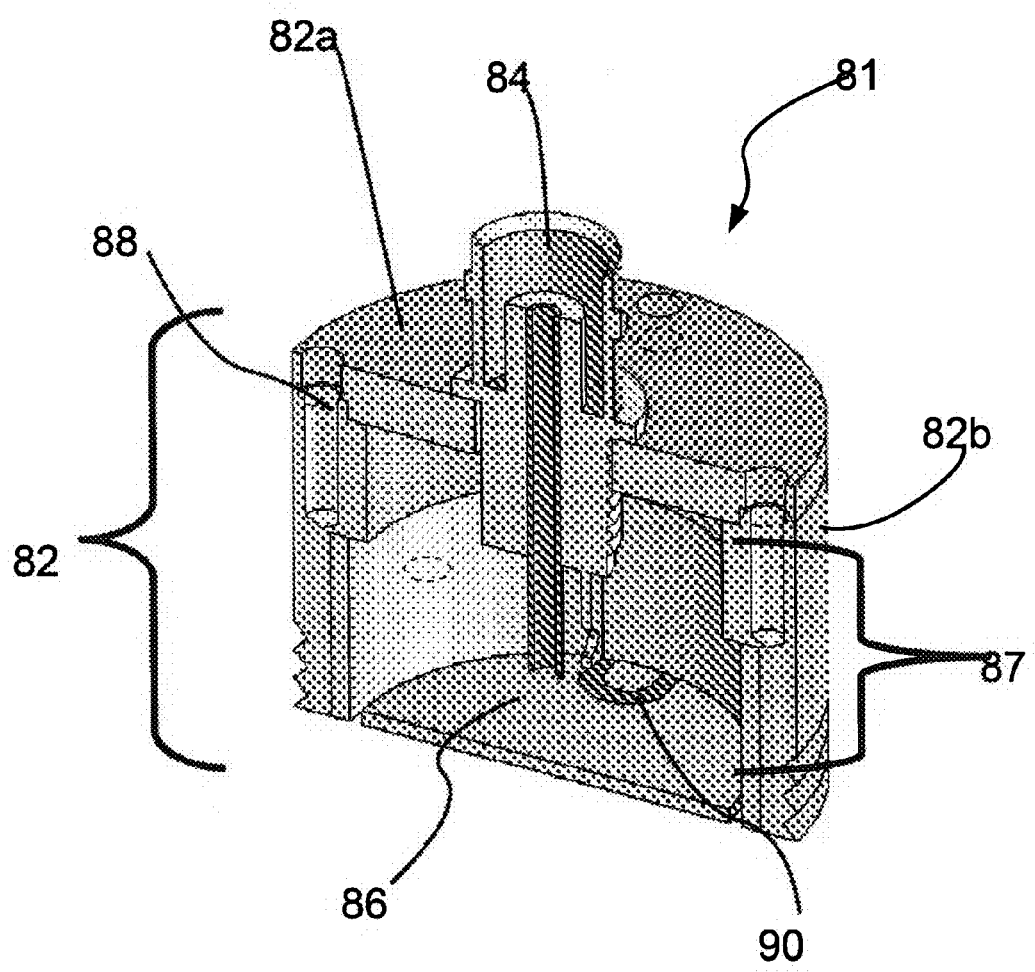
FIG. 11 is a cross-sectional diagram of an ultrasonic transducer of the present disclosure. An air gap is present within the transducer, and no backing layer is present.

FIG. 11 is a cross-sectional view of an ultrasonic transducer 81 of the present disclosure, which can be used with the acoustophoretic device of FIGS. 1-9. Transducer 81 has an aluminum housing 82. A PZT crystal 86 defines the bottom end of the transducer, and is exposed from the exterior of the housing. The crystal is supported on its perimeter by the housing, with a small elastic layer, e.g. silicone or similar material, located between the crystal and the housing.

Screws (not shown) attach an aluminum top plate 82a of the housing to the body 82b of the housing via threads 88. The top plate includes a connector 84 to pass power to the PZT crystal 86. The bottom and top surfaces of the PZT crystal 86 each contain an electrode. A wrap-around electrode tab 90 connects to the bottom electrode and is isolated from the top electrode. Electrical power is provided to the PZT crystal 86 through the electrodes, with the wrap-around tab 90 being the ground connection point. Note that the crystal 86 has no backing layer or epoxy layer as is present in FIG. 5. Put another way, there is an air gap 87 in the transducer between aluminum top plate 82a and the crystal 86. A minimal backing may be provided in some embodiments.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal/piezoelectric material to vibrate higher order modes of vibration (e.g. higher order modal displacement) with little damping. In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines. In the present disclosure, the transducers are driven so that the piezoelectric crystal vibrates in higher order modes of the general formula (m, n), where m and n are independently 1 or greater. In practice, the transducers of the present disclosure will vibrate at higher orders than (1,2).

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. In another embodiment, the backing may be a lattice work that follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface/protective layer to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylxyene) (e.g. Parylene) or other polymer. Organic and biocompatible coatings such as silicone or polyurethane are also contemplated for use as a wear surface.

Figure 12:
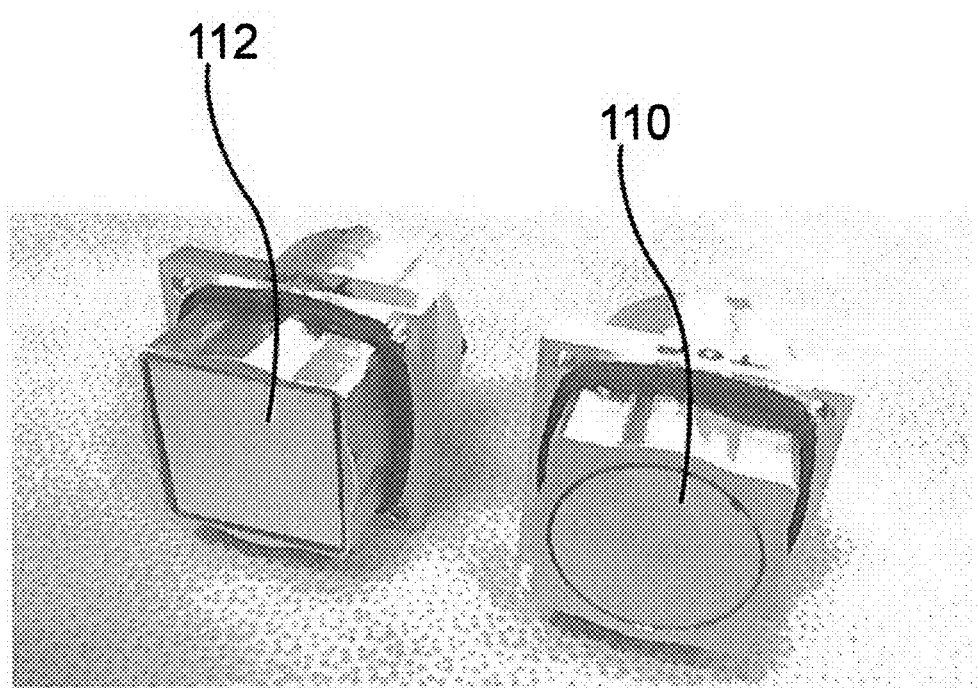
FIG. 12 is a photo of a square transducer and a circular transducer suitable for use in the devices of the present disclosure.

FIG. 12 illustrates two different ultrasonic transducers that can be used in the devices of the present disclosure. The transducer on the right shows a circular-shaped PZT-8 crystal 110 that is 1 inch in diameter. The transducer on the right shows a rectangular-shaped crystal, which here is a square 1 inch by 1 inch crystal. The effect of transducer shape on oil separation efficiency was investigated, and Table 1 shows the results.

TABLE 1

Results of Investigation of Round and Square Transducer Shape

| Transducer Shape | Total Power Input (Watts) | Flowrate (ml/min) | Duration (min) | Capture Efficiency (%) |
|---|---|---|---|---|
| Round | 20 | 500 | 45 | 59% |
| Square | 20 | 500 | 30 | 91% |

The results indicate that the square transducer 112 provides better oil separation efficiencies than the round transducer 110, explained by the fact that the square transducer 112 provides better coverage of the flow channel with acoustic trapping forces, and that the round transducer only provides strong trapping forces along the centerline of the standing wave.

The size, shape, and thickness of the transducer determine the transducer displacement at different frequencies of excitation, which in turn affects oil separation efficiency. Typically, the transducer is operated at frequencies near the thickness resonance frequency (half wavelength). Gradients in transducer displacement typically result in more places for oil to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 13:
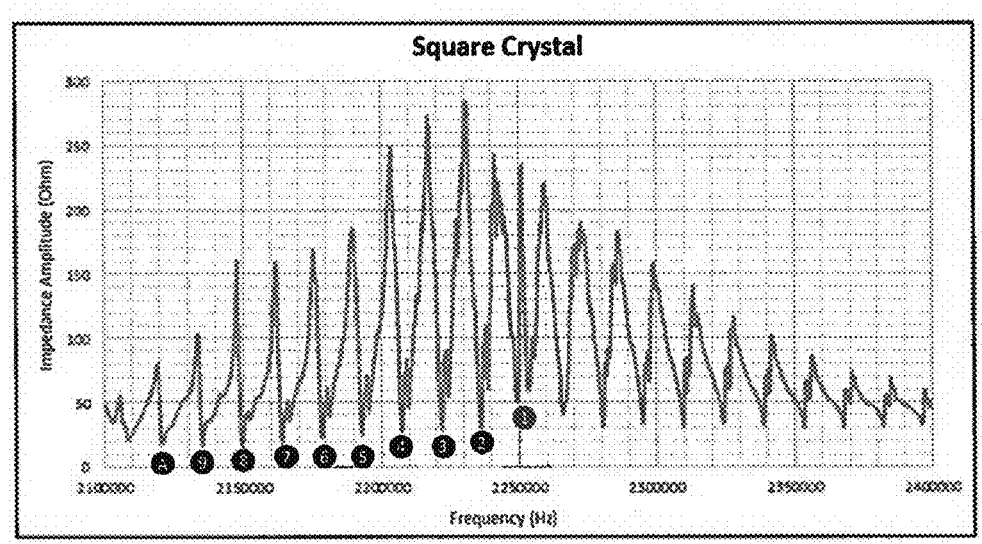
FIG. 13 is a graph of electrical impedance amplitude versus frequency as a square transducer is driven at different frequencies.

FIG. 13 shows the measured electrical impedance amplitude of the transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

To investigate the effect of the transducer displacement profile on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 13, were used as excitation frequencies. The conditions were an experiment duration of 30 min, a 1000 ppm oil concentration, a flow rate of 500 ml/min, and an applied power of 20 W.

Figure 14:
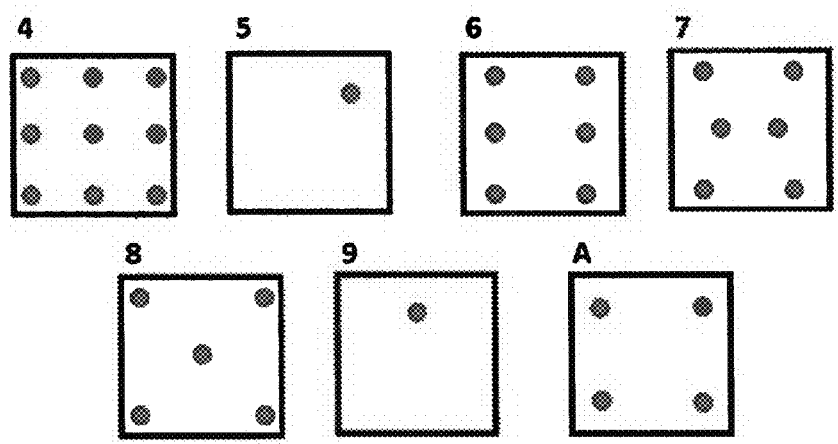
FIG. 14 illustrates the trapping line configurations for seven of the peak amplitudes of FIG. 13.

As the emulsion passed by the transducer, the trapping lines of oil droplets were observed and characterized. The characterization involved the observation and pattern of the number of trapping lines across the fluid channel, as shown in FIG. 14, for seven of the ten resonance frequencies identified in FIG. 13.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five nodal trapping lines are observed. Different displacement profiles of the transducer can produce different (more) trapping lines of the standing waves, with more gradients in displacement profile generally creating higher trapping forces and more trapping lines.

Table 2 summarizes the findings from an oil trapping experiment using a system similar to FIGS. 1-9. An important conclusion is that the oil separation efficiency of the acoustic separator is directly related to the mode shape of the transducer. Higher order displacement profiles generate larger acoustic trapping forces and more trapping lines resulting in better efficiencies. A second conclusion, useful for scaling studies, is that the tests indicate that capturing 5 micron oil droplets at 500 ml/min requires 10 Watts of power per square-inch of transducer area per 1" of acoustic beam span. The main dissipation is that of thermo-viscous absorption in the bulk volume of the acoustic standing wave. The cost of energy associated with this flow rate is 0.667 kWh per cubic meter.

TABLE 2

Trapping Pattern Capture Efficiency Study

| Resonance Peak Location | Total Power Input (Watts) | # of Trapping Lines | Flowrate (ml/min) | Duration (min) | Capture Efficiency (%) |
|---|---|---|---|---|---|
| 4 | 20 | 9 | 500 | 30 | 91% |
| 8 | 20 | 5 | 500 | 30 | 58% |
| A | 20 | 4 | 500 | 30 | 58% |
| 9 | 20 | 2 | 500 | 30 | 37% |

Figure 15:
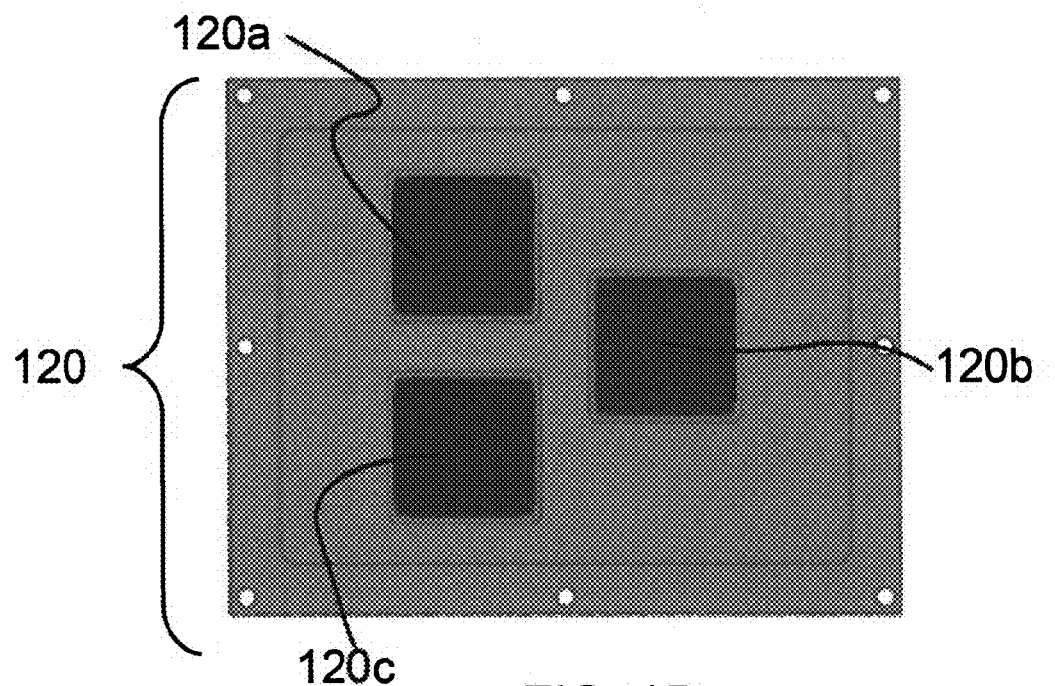
FIG. 15 illustrates a possible array configuration for a group of transducers.
Figure 16:
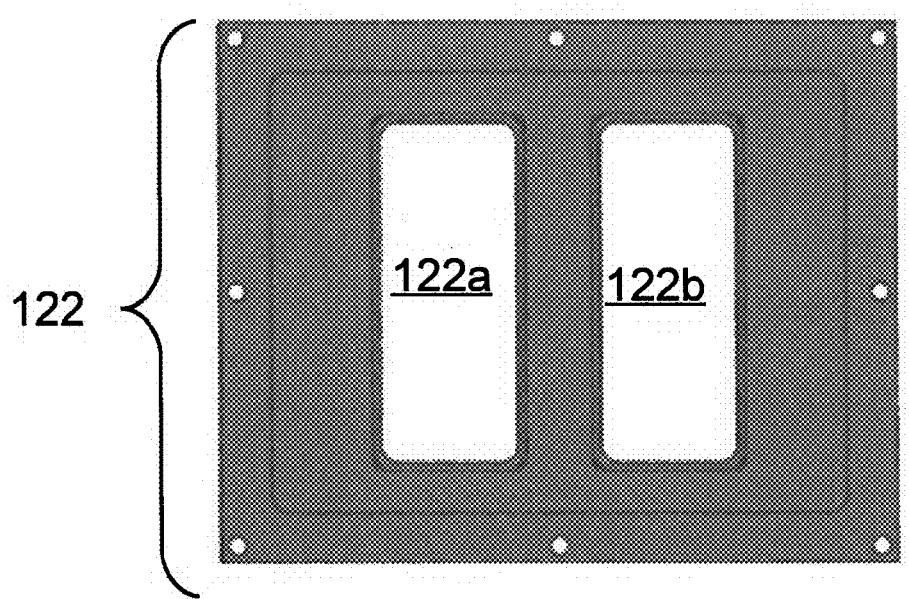
FIG. 16 illustrates another possible array configuration for a group of transducers.

In larger systems, different transducer arrangements are feasible. FIG. 15 shows a transducer array 120 including three square 1"×1" crystals 120a, 120b, 120c. Two squares are parallel to each other, and the third square is offset to form a triangular pattern and get 100% acoustic coverage. FIG. 16 shows a transducer array 122 including two rectangular 1"×2.5" crystals 122a, 122b arranged with their long axes parallel to each other. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired three-dimensional acoustic standing waves.

Figure 17:
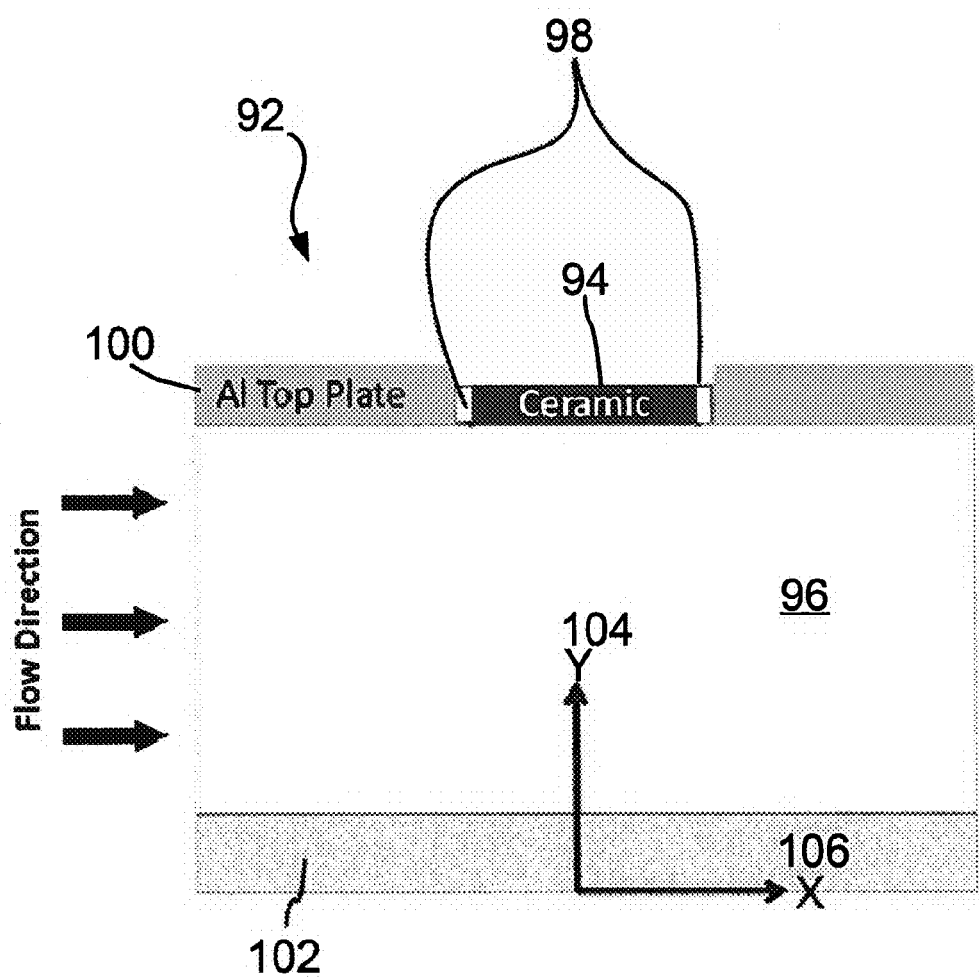
FIG. 17 is a computer model of an acoustophoretic separator simulated to generate FIGS. 18-29.

FIG. 17 is a computer model of an acoustophoretic separator 92 simulated to produce FIGS. 18-29. The piezo ceramic crystal 94 is in direct contact with the fluid in the water channel 96. A layer of silicon 98 is between the crystal 94 and the aluminum top plate 100. A reflector 102 reflects the waves to create standing waves. The reflector is made of a high acoustic impedance material such as steel or tungsten, providing good reflection. For reference, the Y-axis 104 will be referred to as the axial direction. The X-axis 106 will be referred to as the radial or lateral direction. The acoustic pressure and velocity models were calculated in COMSOL including piezo-electric models of the PZT transducer, linear elastic models of the surrounding structure (e.g. reflector plate and walls), and a linear acoustic model of the waves in the water column. The acoustic pressure and velocity was exported as data to MATLAB. The radiation force acting on a suspended particle was calculated in MATLAB using Gor'kov's formulation. The particle and fluid material properties, such as density, speed of sound, and particle size, are entered into the program, and used to determine the monopole and dipole scattering contributions. The acoustic radiation force is determined by performing a gradient operation on the field potential U, which is a function of the volume of the particle and the time averaged potential and kinetic energy of the acoustic field.

Figure 18:
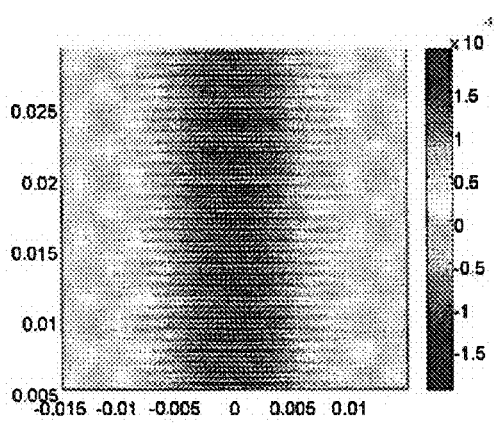
FIG. 18 shows a simulation of the axial forces on a particle in an acoustophoretic separator having a piezoelectric crystal producing a single standing wave.
Figure 19:
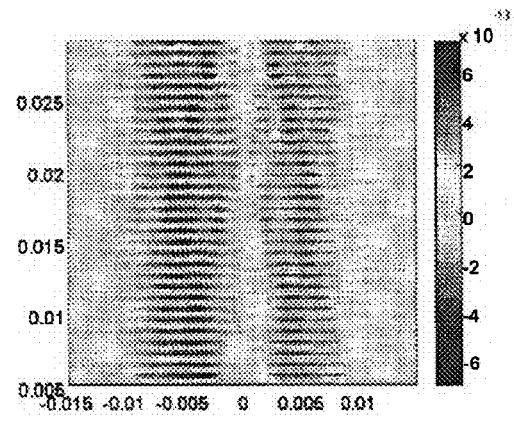
FIG. 19 shows a simulation of the lateral forces on a particle in an acoustophoretic separator having a piezoelectric crystal producing a single standing wave.
Figure 20:
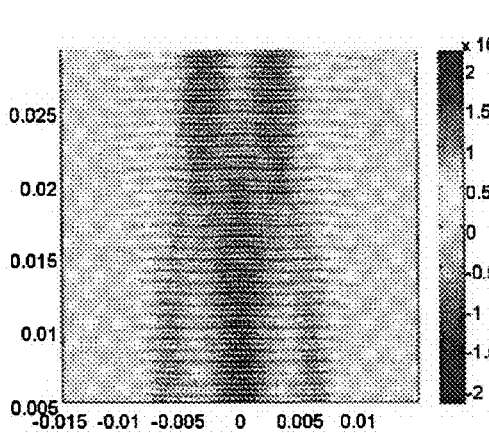
FIG. 20 shows a simulation of the axial forces on a particle in an acoustophoretic separator having a piezoelectric crystal in a multi-mode excitation.
Figure 21:
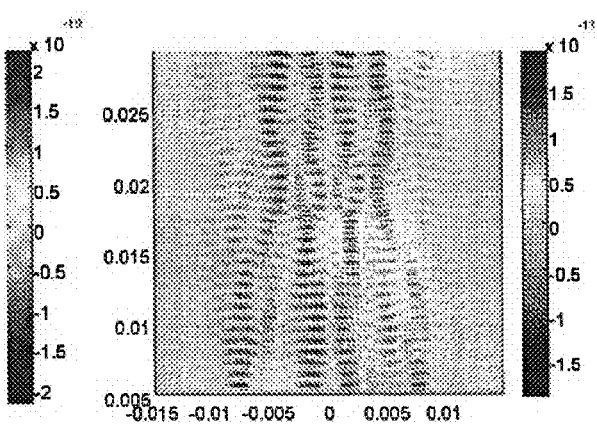
FIG. 21 shows a simulation of the lateral forces on a particle in an acoustophoretic separator a piezoelectric crystal in a multi-mode excitation.

FIGS. 18-21 show simulations of the difference in trapping pressure gradients between a single acoustic wave and a multimode acoustic wave. FIG. 18 shows the axial force associated with a single standing acoustic wave. FIG. 19 shows the lateral force due to a single standing acoustic wave. FIG. 20 and FIG. 21 show the axial force and lateral force, respectively, in a multi-mode (higher order vibration modes having multiple nodes) piezoelectric crystal excitation where multiple standing waves are formed. The electrical input is the same as the single mode of FIG. 18 and FIG. 19, but the trapping force (lateral force) is 70 times greater (note the scale to the right in FIG. 19 compared to FIG. 21). The figures were generated by a computer modeling simulation of a 1 MHz piezo-electric transducer driven by 10 V AC potted in an aluminum top plate in an open water channel terminated by a steel reflector (see FIG. 17). The field in FIG. 18 and FIG. 19 is 960 kHz with a peak pressure of 400 kPa. The field in FIG. 20 and FIG. 21 is 961 kHz with a peak pressure of 1400 kPa. In addition to higher forces, the 961 kHz field has more gradients and focal spots.

Figure 22:
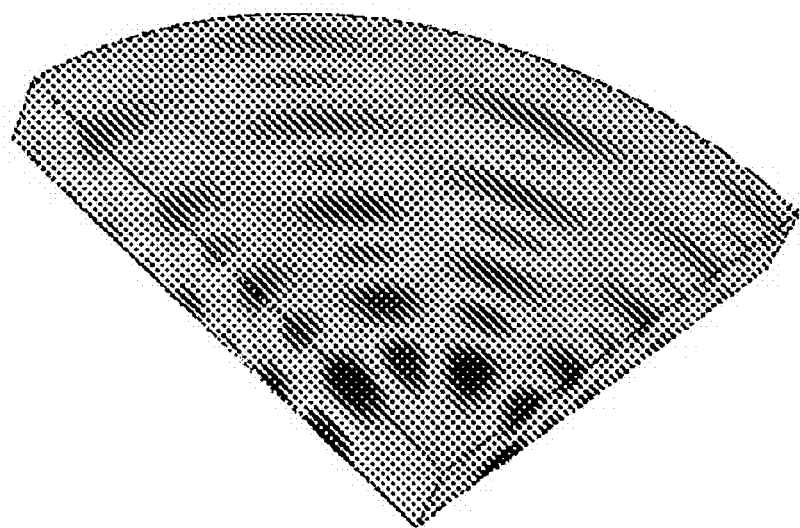
FIG. 22 shows a three dimensional computer generated model of a mode shape calculation for a circular crystal driven at a frequency of 1 MHz.

FIG. 22 shows a three dimensional computer generated model of a mode shape calculation showing the out-of-plane displacement for a circular crystal driven at a frequency of 1 MHz.

FIGS. 23-29 are based on the model of FIG. 17 with a PZT-8 piezo-electric transducer operating at 2 MHz. The transducer is 1" wide and 0.04" thick, potted in an aluminum top plate (0.125" thick) in a 4"×2" water channel terminated by a steel reflector plate (0.180" thick). The acoustic beam spans a distance of 2". The depth dimension, which is 1", is not included in the 2D model. The transducer is driven at 15V and a frequency sweep calculation is done to identify the various acoustic resonances. The results of the three consecutive acoustic resonance frequencies, i.e., 1.9964 MHz (FIGS. 23-25), 2.0106 MHz (FIG. 26 and FIG. 27), and 2.025 MHz (FIG. 28 and FIG. 29), are shown. The acoustic radiation force is calculated for an oil droplet with a radius of 5 micron, a density of 880 kg/m$^3$, and speed of sound of 1700 m/sec. Water is the main fluid with a density of 1000 kg/m$^3$, speed of sound of 1500 m/sec, and dynamic viscosity of 0.001 kg/msec.

Figures 23, 24:
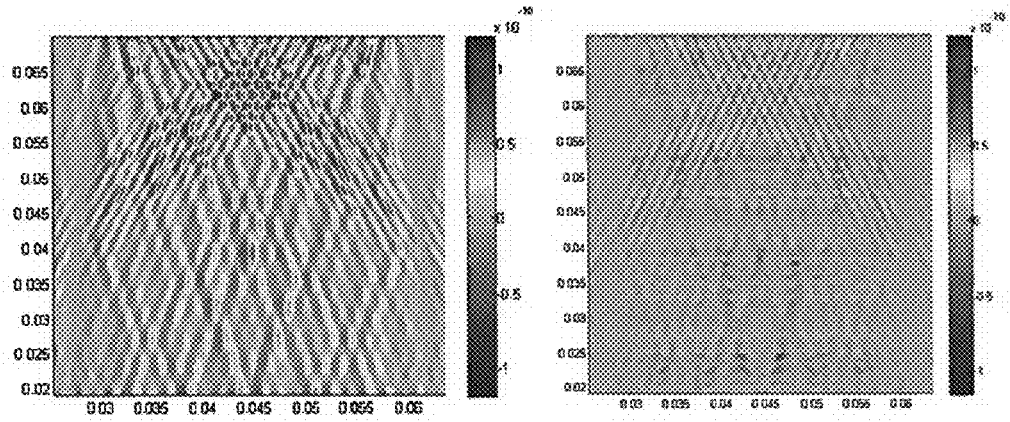
FIG. 23 shows the lateral (horizontal) acoustic radiation force at 1.9964 MHz.
FIG. 24 shows the axial (vertical) component for a resonance frequency of 1.9964 MHz.
Figure 25:
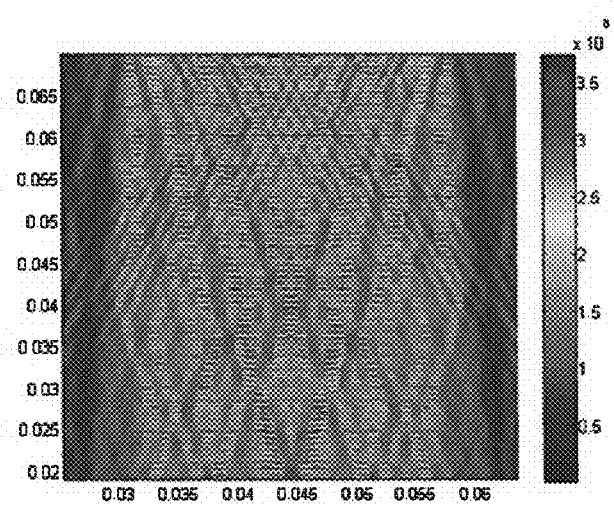
FIG. 25 shows the acoustic pressure amplitude at 1.9964 MHz.

FIG. 23 shows the lateral (horizontal) acoustic radiation force. FIG. 24 shows the axial (vertical) component for a resonance frequency of 1.9964 MHz. FIG. 25 shows the acoustic pressure amplitude. FIG. 23 and FIG. 24 show that the relative magnitude of the lateral and axial component of the radiation force are very similar, about 1.2e-10 N, indicating that it is possible to create large trapping forces, where the lateral force component is of similar magnitude or higher than the axial component. This is a new result and contradicts typical results mentioned in the literature.

A second result is that the acoustic trapping force magnitude exceeds that of the fluid drag force, for typical flow velocities on the order of mm/s, and it is therefore possible to use this acoustic field to trap the oil droplet. Of course, trapping at higher flow velocities can be obtained by increasing the applied power to the transducer. That is, the acoustic pressure is proportional to the driving voltage of the transducer. The electrical power is proportional to the square of the voltage.

A third result is that at the frequency shown, high trapping forces associated with this particular trapping mode extend across the entire flow channel, thereby enabling capture of oil droplets across the entire channel width. Finally, a comparison of the minima of the acoustic trapping force field, i.e., the locations of the trapped particles, with the observed trapping locations of droplets in the standing wave shows good agreement, indicating that COMSOL modeling is indeed an accurate tool for the prediction of the acoustic trapping of particles. This will be shown in more detail below.

FIG. 26 shows the lateral force component at a resonance frequency of 2.0106 MHz, and FIG. 27 shows the axial acoustic radiation force component at a resonance frequency of 2.0106 MHz. FIG. 26 and FIG. 27 exhibit higher peak trapping forces than FIG. 23 and FIG. 24. The lateral acoustic radiation forces exceed the axial radiation force. However, the higher trapping forces are located in the upper part of the flow channel, and do not span the entire depth of the flow channel. It would therefore represent a mode that is effective at trapping particles in the upper portion of the channel, but not necessarily across the entire channel. Again, a comparison with measured trapping patterns indicates the existence of such modes and trapping patterns.

FIG. 28 shows the lateral force component at a resonance frequency of 2.025 MHz, and FIG. 29 shows the axial acoustic radiation force component at a resonance frequency of 2.025 MHz. The acoustic field changes drastically at each acoustic resonance frequency, and therefore careful tuning of the system is critical. At a minimum, 2D models are necessary for accurate prediction of the acoustic trapping forces.

2D axisymmetric models were developed to calculate the trapping forces for circular transducers. The models were used to predict acoustic trapping forces on particles, which can then be used to predict particle trajectories in combination with the action of fluid drag and buoyancy forces. The models clearly show that it is possible to generate lateral acoustic trapping forces necessary to trap particles and overcome the effects of buoyancy and fluid drag. The models also show that circular transducers do not provide for large trapping forces across the entire volume of the standing wave created by the transducer, indicating that circular transducers only yield high trapping forces near the center of the ultrasonic standing wave generated by the transducer, but provide much smaller trapping forces toward the edges of the standing wave. This further indicates that the circular transducer only provides limited trapping for a small section of the fluid flow that would flow across the standing wave of the circular transducer, and no trapping near the edges of the standing wave.

Figure 30:
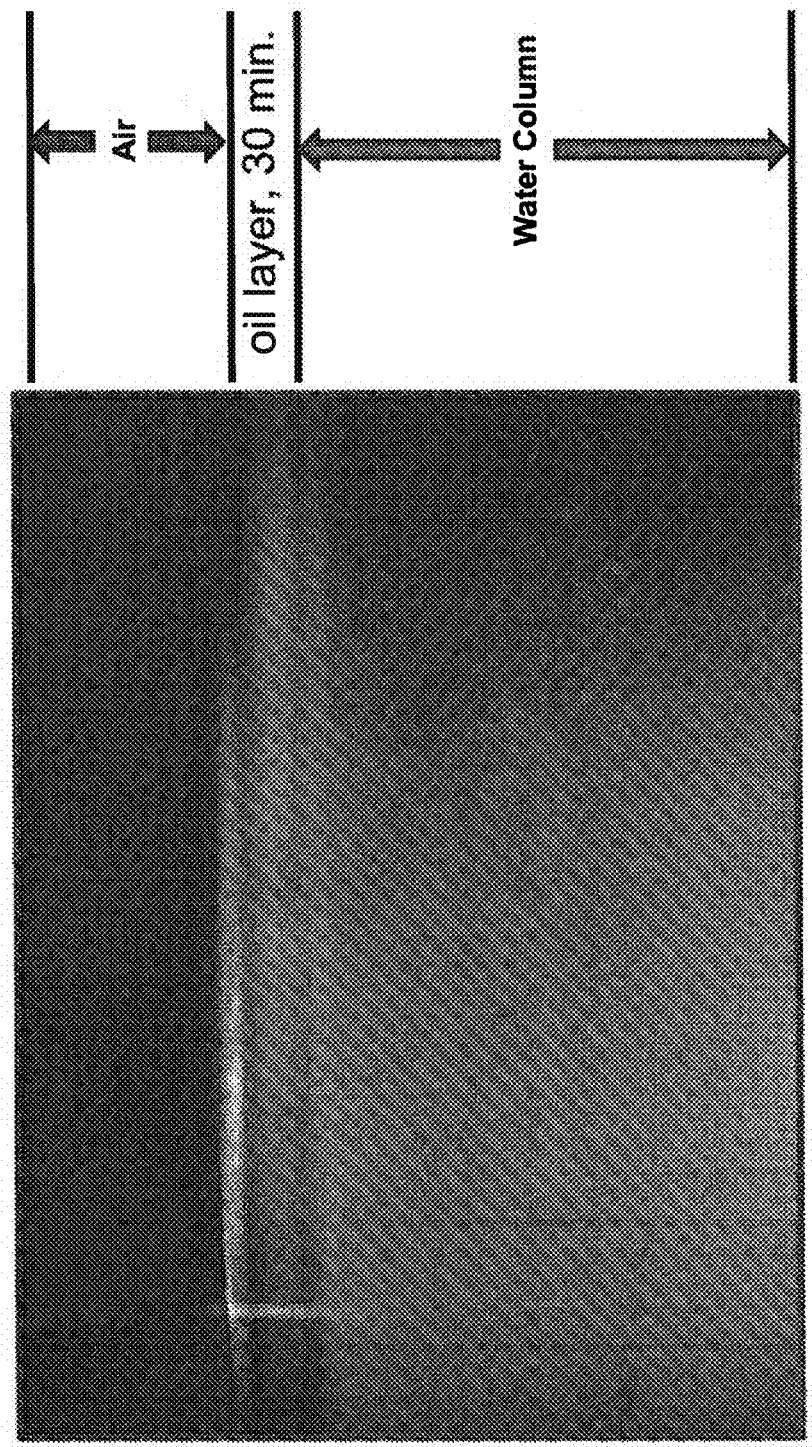
FIG. 30 is a picture showing the results of an oil/water separation experiment.

FIG. 30 is a picture showing the separation attained by an apparatus of FIGS. 1-9 after 30 minutes of operation. This picture is taken in a column attached to the first device outlet. An air layer is present at the top, followed by an oil layer and a water column. The oil is clearly separated from the water column.

The acoustophoretic devices of the present disclosure create a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits better particle trapping and collection in the flow chamber and along well-defined trapping lines, as opposed to merely trapping particles in collection planes as in conventional devices. The particles have significant time to move to nodes or anti-nodes of the standing waves, generating regions where the particles can concentrate, agglomerate, and/or coalesce.

In some embodiments, the fluid flow has a Reynolds number of up to 500, i.e. laminar flow is occurring. For practical application in industry, the Reynolds number is usually from 10 to 500 for the flow through the system. The particle movement relative to the fluid motion generates a Reynolds number much less than 1.0. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow. The flow of molasses is an example.

Wall contouring and streamlining have very lithe importance to the flow of very viscous fluids or the flow in very tiny passages, like MEMS devices. The flow of the particles relative to the fluid in MEMS devices will be Stokes flow because both the particle diameters and the relative velocities between the particles and fluid are very small. On the other hand, the Reynolds number for the flow through the present system will be much greater than 1.0 because the fluid velocity and inlet diameter are much larger. For Reynolds numbers much greater than 1.0, viscous forces are dominant only where the flow is in contact with the surface. This viscous region near the surface is called a boundary layer and was first recognized by Ludwig Prandtl (Reference 2). In duct flow, the flow will be laminar if the Reynolds number is significantly above 1.0 and below 2300 for fully developed flow in the duct. The flow velocity starts off uniform. As the flow moves down the duct, the effect of wall viscous forces will diffuse inward towards the centerline to generate a parabolic velocity profile. This parabolic profile will have a peak value that is twice the average velocity. The length required for the parabolic profile to develop is a function of the Reynolds number. For a Reynolds number of 20, the development length will be 1.2 duct diameters. Thus, fully developed flow happens very quickly. This peak velocity in the center can be detrimental to acoustic particle separation. Also, turbulence can occur and so flow surface contouring is very important in controlling the flow. Thus, the shape of the contoured nozzle wall will have a large effect on the final velocity profile. The area convergence increases the flow average velocity, but it is the wall contour that determines the velocity profile. The nozzle wall contour will be a flow streamline, and is designed with a small radius of curvature.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer and the reflector. Such hot spots are located in the maxima or minima of acoustic radiation potential. Such hot spots represent particle collection locations which allow for better wave transmission between the transducer and the reflector during collection and stronger inter-particle forces, leading to faster and better particle agglomeration.

In biological applications, many parts, e.g. the tubing leading to and from the device, may all be disposable, with only the transducer and reflector to be cleaned for reuse. Avoiding centrifuges and filters allows better separation of cells without lowering the viability of the cells. The form factor of the acoustophoretic device is also smaller than a filtering system, allowing cell separation to be miniaturized. The transducers may also be driven to create rapid pressure changes to prevent or clear blockages due to agglomeration of cells. The frequency of the transducers may also be varied to obtain optimal effectiveness for a given power.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoresis device for continuously separating a second fluid or a particulate from a host fluid, comprising:
    one or more device inlets at a first end of the device, the first end having a first diameter for receiving fluid flow;
    a contoured wall downstream of the inlet that narrows the fluid flow to a second diameter of a connecting duct;
    a flow chamber downstream of the connecting duct, the flow chamber having:
        an inlet at a first end for receiving the fluid flow,
        an outlet at a second end opposite the first end,
        at least one ultrasonic transducer located on a wall of the flow chamber, the ultrasonic transducer including a piezoelectric material driven by a voltage signal to create a multi-dimensional standing wave in the flow chamber that results in an acoustic radiation force having an axial force component and a lateral force component that are of the same order of magnitude, and a reflector located on a wall on the opposite side of the flow chamber from the at least one ultrasonic transducer;

a first device outlet located at the first end of the device and separated from the device inlet by a longitudinal sidewall; and a second device outlet located at a second end of the device downstream of the flow chamber outlet;

wherein the second fluid or particulate is continuously trapped in the standing wave, then agglomerates, aggregates, clumps, or coalesces into larger particles, and eventually rises or settles out of the host fluid due to buoyancy or gravity forces, and exits the flow chamber.

2. The device of claim 1, wherein the device includes a plurality of device inlets spaced about the first end of the device, and the longitudinal sidewall is spaced apart from the contoured wall.

3. The device of claim 1, wherein the piezoelectric material of the at least one ultrasonic transducer has a rectangular shape.

4. The device of claim 1, wherein the reflector has a non-planar surface.

5. The device of claim 1, wherein the first end of the device has a circular cross-section and the flow chamber has a rectangular cross-section.

6. The device of claim 1, wherein the transducer comprises:

a housing having a top end, a bottom end, and an interior volume; and a crystal at the bottom end of the housing having an exposed exterior surface and an interior surface, the crystal being able to vibrate when driven by a voltage signal.

7. The device of claim 6, wherein no backing layer is present within the housing of the transducer, and an air gap is present in the interior volume between the crystal and a top plate at the top end of the housing.

8. The device of claim 6, wherein the transducer further comprises a backing layer contacting the interior surface of the crystal, the backing layer being made of a substantially acoustically transparent material.

9. The device of claim 8, wherein the substantially acoustically transparent material is balsa wood, cork, and foam.

10. The device of claim 8, wherein the substantially acoustically transparent material has a thickness of up to 1 inch.

11. The device of claim 1, wherein the flow chamber further comprises a transparent window for viewing the interior of the flow chamber.

12. The device of claim 1, wherein the device has a length L from the at least one device inlet to a bottom of the longitudinal sidewall, and a ratio of the length L to the first diameter is less than 1.

13. The device of claim 1, wherein the flow chamber has a plurality of the ultrasonic transducers located on the wall of the flow chamber.

* * * * *

UNITED STATES PATENT AND TRADEMARK OFFICE
CERTIFICATE OF CORRECTION

PATENT NO.       : 9,272,234 B2
APPLICATION NO.  : 13/943529
DATED            : March 1, 2016
INVENTOR(S)      : Bart Lipkens et al.

Page 1 of 1

It is certified that error appears in the above-identified patent and that said Letters Patent is hereby corrected as shown below:

Title page, item (72) Inventors: Should read as follows
Bart Lipkens, Hampden, MA (US);
Jason Dionne, Simsbury, CT (US);
Ari Mercado, Agawam, MA (US);
Brian Dutra, East Longmeadow, MA (US);
Walter M. Presz, Jr., Wilbraham, MA (US);
Thomas J. Kennedy, III, Wilbraham, MA (US);
Louis Masi, Wilbraham, MA, (US)

Signed and Sealed this
Third Day of May, 2016

Michelle K. Lee
*Director of the United States Patent and Trademark Office*